United States Patent
Chase et al.

(10) Patent No.: US 11,819,485 B2
(45) Date of Patent: *Nov. 21, 2023

(54) LEVODOPA FRACTIONATED DOSE COMPOSITION AND USE

(71) Applicant: AVION PHARMACEUTICALS, LLC, Alpharetta, GA (US)

(72) Inventors: Thomas N. Chase, Washington, DC (US); Kathleen E. Clarence-Smith, Washington, DC (US)

(73) Assignee: AVION PHARMACEUTICALS, LLC, Alpharetta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/896,808

(22) Filed: Aug. 26, 2022

(65) Prior Publication Data

US 2023/0233496 A1    Jul. 27, 2023

Related U.S. Application Data

(63) Continuation of application No. 17/219,253, filed on Mar. 31, 2021, now Pat. No. 11,439,613, which is a continuation of application No. 16/719,203, filed on Dec. 18, 2019, now Pat. No. 11,033,521, which is a continuation of application No. PCT/US2019/024464, filed on Mar. 28, 2019.

(60) Provisional application No. 62/650,012, filed on Mar. 29, 2018.

(51) Int. Cl.
  *A61K 31/197*    (2006.01)
  *A61K 9/00*    (2006.01)
  *A61K 9/24*    (2006.01)

(52) U.S. Cl.
  CPC .......... *A61K 31/197* (2013.01); *A61K 9/0053* (2013.01); *A61K 9/209* (2013.01)

(58) Field of Classification Search
  CPC ..... A61K 31/197; A61K 9/0053; A61K 9/209
  See application file for complete search history.

(56) References Cited

U.S. PATENT DOCUMENTS

| | | |
|---|---|---|
| 5,061,494 A | 10/1991 | Ni et al. |
| 7,838,031 B2 | 11/2010 | Solomon et al. |
| 7,879,352 B2 | 2/2011 | Solomon et al. |
| 8,158,148 B2 | 4/2012 | Solomon et al. |
| 8,231,902 B2 | 7/2012 | Solomon et al. |
| 8,506,999 B2 | 8/2013 | Solomon et al. |
| 2008/0233189 A1 | 9/2008 | Solomon et al. |

OTHER PUBLICATIONS

Spielberger et al. "Invasive Treatment Strategies in a Patient with PARK 15—Associated Parkinsonism" Movement Disorders Clinical Practice, Jul. 25, 2015, pp. 434-435 (Year: 2015).*
Cloud et al. "Treatment strategies for dystonia" Expert Opin. Pharmacother. (2010) 11(1):5-15 (Year: 2010).*
Sinemet (https://www.rxlist.com/sinemet-cr-drug.htm) available online Oct. 25, 2008 (Year: 2008).*
Sabine Spielberger, et al., "Invasive Treatment Strategies in a Patient with PARK 15—Associated Parkinsonism", Movement Disorders Clinical Practice, Jul. 25, 2015, pp. 434-435.
Leslie J. Cloud, MD, et al., "Treatment Strategies for Dystonia", Expert Opinion on Pharmacotherapy, Jan. 2010, 17 pages, vol. 11, No. 1.
Emilio Fernandez-Alvarez, et al., "Paediatric Movement Disorders", John Libbey Eurotext, 2005, p. 66.
J. Eric Ahlskog, PhD, MD, "Cheaper, Simpler, and Better: Tips for treating Seniors with Parkinson Disease", Mayo Clinic Proceedings, Dec. 2011, pp. 1211-1216, vol. 86, No. 12.
Novartis, "Stalevo 100 (Carbidopa, Entacapone and Levodopa) Tablet Label", FDA, Sep. 28, 2010, 32 pages.
Lori M. Dickerson, "Treatment of Early Parkinson's Disease", American Family Physician, Aug. 1, 2005, 7 pages.
Livia Dezsi, MD, et al., "Clinical implications of irregular ADMET properties with levodopa and other antiparkinson's drugs", Department of Neurology, University of Szeged, Aug. 14, 2017, 37 pages.
International Search Report for PCT/US2019/024464 dated Jun. 20, 2019 [PCT/ISA/210].

* cited by examiner

*Primary Examiner* — Andrew S Rosenthal
(74) *Attorney, Agent, or Firm* — Sughrue Mion, PLLC

(57) ABSTRACT

There is provided a convenient new treatment of Parkinson disease by a frequent administration of optimal levodopa doses mimicking a continuous intravenous or infusion treatment, thus mitigating motor complications; and a new carbidopa/levodopa pharmaceutical unit form providing said new treatment.

44 Claims, No Drawings

LEVODOPA FRACTIONATED DOSE COMPOSITION AND USE

CROSS REFERENCE TO RELATED APPLICATIONS

This application is a continuation of U.S. application Ser. No. 17/219,253, filed Mar. 31, 2021 (allowed), which is a continuation of U.S. application Ser. No. 16/719,203, filed Dec. 18, 2019 (now U.S. Pat. No. 11,033,521, issued on Jun. 15, 2021), which is a Bypass Continuation of International Application No. PCT/US2019/024464, filed Mar. 28, 2019, which claims the benefit of U.S. Provisional Patent Application No. 62/650,012, filed Mar. 29, 2018.

FIELD OF THE INVENTION

The present invention pertains to the field of the treatment of Parkinson's disease and of levodopa-responsive syndromes in children.

OBJECT OF THE INVENTION

The present invention concerns a novel approach in the carbidopa/levodopa oral treatment of Parkinson's disease, mimicking the intravenous infusion. Said improved treatment is made by using a novel, multiscored, bilayered carbidopa25 mg/levodopa100 mg pharmaceutical unit form that enables precise dose fractionation to delay and even avoid the onset of motor response complications in early stage patients, reduce the severity of these complications in mid-stage patients, and safely treat or even eliminate existing motor response complications in late-stage patients.

Furthermore, this multiscored, bilayered tablet meets the treatment needs of hypersensitive early-stage parkinsonian patients and of children suffering from levodopa-responsive syndromes.

Definitions

"AADC": Amino Acid Decarboxylase.
"CNS": Central Nervous System.
"PD": Parkinson's Disease.
"RLS": Restless Leg Syndrome.
"DRD" Dopa-Responsive Dystonia.
"MRCs": Motor Response Complications.
"PNS": Peripheral Nervous System.
"CD": Carbidopa.
"LD": Levodopa.
"CD/LD": Combination of carbidopa and levodopa.
"CD/LD Standard treatment": the administration instructions given in the prescription labels of the Health Authorities.
According to the Sinemet® U.S.A. label, "the treatment is best initiated with one tablet of CD/LD 25/100 three times a day. This dosage schedule provides 25 mg of CD per tablet, equivalent to 75 mg per day on a typical 3 times per day daily dosing schedule. Dosage may be increased by one tablet every day or every other day, as necessary to a dosage which may extend as high as eight tablets of CD/LD 25/100 per day. In some cases, a CD/LD 25/250 tablet may be used and the dosage of CD/LD 25-250 may be increased by one-half or one tablet every day or every other day to a maximum of eight tablets per day.
According to the 19 Oct. 2017 revision of the SINEMET® 12.5 mg/50 mg Tablets, SINEMET® 10 mg/100 mg Tablets, SINEMET® Plus 25 mg/100 mg Tablets and SINEMET® 25 mg/250 mg Tablets prescription label (Merck Sharp & Dohme Limited UK), "dosage may be best initiated with one tablet of 'Sinemet Plus 25 mg/100 mg' three times a day. This dosage schedule provides 75 mg of CD per day. Dosage may be increased by one tablet of 'Sinemet 12.5 mg/50 mg' or 'Sinemet Plus 25 mg/100 mg' every day or every other day, as necessary, until a dosage equivalent of eight tablets of 'Sinemet Plus 25 mg/100 mg' a day is reached. If 'Sinemet 10 mg/100 mg Tablets' or 'Sinemet 12.5 mg/50 mg Tablets' are used, dosage may be initiated with one tablet three or four times a day. Titration upward may be required in some patients to achieve optimum dosage of CD. The dosage may be increased by one tablet every day or every other day until a total of eight tablets (two tablets q.d.s.) is reached. Response has been observed in one day, and sometimes after one dose. Fully effective doses usually are reached within seven days as compared to weeks or months with LD alone. 'Sinemet 12.5 mg/50 mg Tablets' or 'Sinemet 10 mg/100 mg Tablets' may be used to facilitate dosage titration according to the needs of the individual patient".

"Multiscore tablet": a bilayered tablet consisting of a two-score or three-score top layer comprising CD/LD in a total amount of 25 mg/100 mg, in admixture with a pharmaceutical carrier, a bottom layer comprising a pharmaceutical carrier without active ingredient, and wherein each score of said top layer penetrates said bottom layer without cutting it.

"Section": each part of the multiscore tablet obtained by breaking said multiscore tablet, each containing an equal unit dose of CD/LD.

"Unit dose": a single section of the multiscore tablet comprising a specific amount of CD/LD selected from the group consisting of 6.25 mg/25 mg and 8.(3) mg/33,(3) mg, in admixture with a pharmaceutical carrier.

"Single dose" a CD/LD dose consisting of from one to six unit doses, to be simultaneously administered to a patient.

BACKGROUND OF THE INVENTION

Parkinson's disease (PD) and related movement disorders are now estimated to affect nearly 1.5 million in the U.S. It is thought that approximately 7 to 10 million are living with this disorder worldwide. Some 60,000 Americans are diagnosed with PD each year, a number that does not reflect the thousands of cases that go undetected. The incidence of PD increases with age, although an estimated four percent of people with this disorder are diagnosed before the age of 50. Rarely, children can develop a juvenile form of PD. Men are 1.5-times more likely to have PD than women. The combined direct and indirect cost of PD, including treatment, social security payments and lost income from inability to work, has been calculated to be nearly $25 billion per year in the U.S. alone. As time passes, the burden of PD will increase with the aging of the population, and become unsustainable.

PD is considered a neurodegenerative disorder of unknown etiology with onset generally after the age of 60 years. Symptoms affect both motor and non-motor functions and gradually, yet inexorably, progress. Motor symptoms classically include tremor, muscle rigidity and a generalized bradykinesia. Gait and balance are often affected. Non-motor symptoms reflect a broad range of central and peripheral nervous systems involvement. Progression is relentless, leading to profound disability and ultimately death within some 10 to 20 years.

The degenerative process is now generally attributed to a neurotoxic product of the aberrant processing of an intraneuronal protein called synuclein. As a result, a number of neuronal systems become injured and eventually die. The synthesis and release of chemical transmitters from the affected neurons gradually declines and normal function diminishes. A deficiency in dopamine (DA)-mediated neurotransmission is the major contributor to the motor abnormalities associated with PD. Pharmaceuticals that act to correct this deficit in brain thus constitute the mainstay of current therapy.

Currently approved treatments for PD confer symptomatic benefit to motor dysfunction, but do not affect onset or progression of the underlying disease process. All act by stimulating dopaminergic transmission in brain by either increasing transmitter availability or by directly simulating its postsynaptic dopamine receptors.

The administration of LD, the direct precursor of dopamine, acts to restore the diminished levels of dopamine in the brain of PD patients. Most of these drugs were discovered years ago, although some have been subject to minor subsequent improvements. For the past 50 years a combination of LD and CD (Sinemet®) has served as the gold standard of PD treatment. No other medication has been found to be more effective.

As set forth in the Definitions, according to the standard treatment (Sinemet® USA label), the CD/LD combination used in the PD therapy is CD/LD 10 mg/100 mg, CD/LD 25 mg/100 mg, or CD/LD 25/250, initially generally administered three times per day.

In the UK, according to the 19 Oct. 2017 revision, the CD/LD 12.5 mg/50 mg, 10 mg/100 mg, 25 mg/100 mg and 25 mg/250 mg Tablets prescription label (Merck Sharp & Dohme Limited UK), said tablet may be administered four times a day.

Normally, the standard treatment, herein below also referred to as "standard administration schedule", is practiced worldwide, compatibly with the individual needs of the PD patients. For example, the timing of doses may vary between patients and stage of the disease, generally getting shorter as the disease progresses. According to the current standard treatment and single doses, this timing of doses represents a further problem that is unresolved.

Unfortunately, chronic standard treatment with LD and its various congeners eventually produces adverse reactions, especially motor response complications (MRCs). These have been attributed to the non-physiologic, pulsatile, manner in which currently available oral medications stimulate striatal dopamine receptors. Long-term, periodic, high-intensity stimulation of these receptors inevitably leads to down-stream striatal changes that favor the appearance of MRCs. These adverse events reflect a progressive shortening of the response duration, narrowing of the therapeutic window, and unrelenting involuntary movements affecting limbs, trunk and face, which appear in nearly 50% of patients within 5 years and in some 90% within 10 years of treatment initiation. Ultimately, these MRCs tend to become more disabling than the original parkinsonian symptoms.

Preclinical and clinical studies indicate that chronic dopaminergic treatments that act to strongly and intermittently stimulate postsynaptic dopamine receptors in brain are more likely to induce earlier and more severe MRCs (Chase et al., 1989; Papa et al. 1994; Bibbiani et al., 2005; Mouradian et al., 1987; 1990). In contrast, the administration of lower, more frequent (and thus virtually continuous) doses appear to carry a lower risk of causing these debilitating complications and a higher probability of alleviating those that have already become manifest (Papa et al. 1994; Bibbiani et al., 2005; Mouradian et al., 1987; 1990). These responses presumably reflect the fact that brain dopamine receptors are normally exposed to continual (not pulsatile) stimulation by concentrations of the transmitter amine held within the physiologic range (not intermittent, high-level peaks).

The short plasma half-life of LD (approximately 90 min) contributes to the development of MRCs. Standard administration schedules produce high peak concentrations of DA newly synthesized from each dose of LD. In early stage disease, these peaks tend to be smoothed out by the storage capacity of residual dopaminergic neurons (Chase., 1989). But with disease progression these neurons degenerate and the pulsatile nature of DA produced by the periodic administration of standard LD formulations translates into pulsatile release of DA onto its postsynaptic receptors. Long-term exposure to this non-physiologic stimulation is now believed to be a major contributor to the appearance of motor complications (Chase et al., 1989, 1993, 1994).

Parkinson's disease symptoms start becoming apparent when patients have lost about 60% of their nigral nerve cells (Chase et al, 1989, 1993, 1994). At the beginning of the disease, DA formed in the brain from orally administered LD is stored in the nerve terminals of the substantia nigra nerve cells. Storage allows for slow and regulated release of DA, explaining the 6-hour duration of effect of each LD dose.

As PD progresses, an increasing number of DA nerve cells die out, fewer nerve terminals are available for DA storage. As a consequence, the duration of effect of each dose becomes shorter, decreasing from approximately 6 hours in the early stages of the disease to ultimately about 1.5 hours (the half-life of LD in the blood stream). Furthermore, DA is no longer released in a regulated fashion. Each LD dose produces a huge DA peak at its postsynaptic receptors that causes dyskinesias, and a little later, intrasynaptic levels of DA fall below the physiologic range and all the motor symptoms of PD return (wearing off). Patients need treatments that put them constantly in the full "efficacy with no MRCs" plasma (and thus brain) concentration range, but satisfactory oral treatments of this type do not currently exist.

Interestingly, a study in PD patients who received LD only when their disease was very advanced (i.e., very few terminals left for DA storage) showed that these patients developed MRCs within a few weeks of starting LD treatment, demonstrating that MRCs are associated with the degree of nerve cell loss in the nigra and not with duration of LD treatment.

Research conducted at the U.S.A. National Institute of Health and subsequently reproduced throughout the World, showed that when patients were given a steady intravenous dose of LD (CD was given orally) so that the plasma concentrations of LD remained within the full "efficacy with no MRCs" range, patients experienced a full antiparkinsonian effect (no wearing off) without any dyskinesias as long as the infusion lasted (Mouradian et al., 1987; 1990). These results demonstrate that the occurrence of dyskinesias and wearing-off are linked to the pulsatile nature of the oral administration of LD in a situation where there is a profound loss of the storage capacity of residual nigral dopaminergic neurons.

Further research showed that when a round-the-clock 10-day LD infusion was stopped, MRCs returned but were found to have substantially improved, suggesting that if patients could be treated from the early stages of their disease with continuous LD, they might never develop MRCs (Chase et al., et al., 1994). Results in a non-human primate model of PD support this conclusion. A practical means to provide LD therapy would surely transform the prognosis of all those suffering from this cruel disorder. Unfortunately, LD administered intravenously destroys veins, and round-the-clock infusions that last longer than 10 days are not possible.

In conclusion, numerous laboratory and clinical studies have shown that more natural regimen of DA replacement (i.e., the more continuous administration of optimal doses) will provide immediate benefit to Parkinson patients and will delay the onset and reduce the severity of MRCs in early- and mid-stage patients; in late stage individuals, continuous dopaminomimetic therapy can reduce the severity or even eliminate existing MRCs (Chase et al., 1994).

Researchers have tried to find ways to deliver LD continuously to those with PD and related disorders. Over the years, many attempts have been made to provide continuous delivery of CD/LD, but all have failed or provided no more than marginal benefit. A patch could seem to be the obvious response, but the daily dose of LD is too high to fit a patch. A pump to deliver LD continuously was also not possible because levodopa is poorly soluble in water, and the volume to be administered is too large. Attempts at making solutions of levodopa from which patients could drink at frequent intervals, proved impractical and unpopular. Extended release and slow release formulations also failed to provide a clinically useful benefit, because LD can only be absorbed from a very short segment of the duodenum.

More recently, Duodopa, a system whereby a reservoir containing a gel of Sinemet is linked to a catheter that is placed in the duodenum and delivers Sinemet continuously into the gut, was developed and commercialized. Patients on Duodopa have a stable antiparkinsonian response to treatment, with little dyskinesias or wearing-off. However, Duodopa treatment is expensive, requiring surgery to place the intra-duodenal catheter, and complications such as infections or catheter displacement or blockage occur. Duopa Package Insert, Abbvie Inc., January 2015, the disclosure of which is herein incorporated by reference in its entirety. Thus, Duodopa treatment is reserved to few, relatively advanced patients.

US 2007/0190147, US 2007/0031488 (US 2009/0130207), US 2007/0031494, US 2007/0134321, US 2008/0003285, US 2008/0199521, and US 2008/0233189 patent documents, the disclosures of which are incorporated herein in their entirety for reference, disclose a compressed immediate release, multilayer pharmaceutical tablet core structure which comprises two or three or more segments wherein a first scored segment contains a pharmacologically effective amount of a drug or drugs and a second segment, that adjoins said first segment, that may be either inert, i.e. composed of a pharmaceutical carrier only, or may be without any active ingredient, and a possible third segment comprising another active ingredient.

For instance, the US 2008/0233189 patent document discloses a layered tablet having three segments (each defined as "unit dose" in the above definitions): a top segment (top layer according to the present description) comprising at least one active ingredient, an inner or middle segment (layer) containing no active ingredient, and a bottom end segment (layer) comprising a different active ingredient. Said document states that the number of unitary segments (unit doses) formed from a layer of said tablet is not limited to two and that said tablet can have three parallel scores or two crossing scores. According to this document, one outer active segment (layer) of a tablet could contain LD and CD, and the other outer active segment (layer) could contain entacapone, thus providing a three-layer segment comprising three drugs.

However, this document does not give any other information about the possibility of using the CD/LC/entacapone described therein for efficaciously treating PD symptoms as well as preventing and mitigating existing MRCs.

Thus, at the present time, after 50 years of CD/LD standard treatment and almost ten years after the disclosure of US 2008/0233189, the aforementioned problems linked to the use of CD/LD for the treatment with of PD and to the serious consequences deriving from this treatment remain unresolved.

SUMMARY OF THE INVENTION

Early stage PD patients can be successfully treated clinically with any of several currently available CD/LD preparations.

But even though this treatment is highly successful in reducing or even eliminating all parkinsonian symptoms, they risk hidden damage to downstream striatal systems, changes that favor the later appearance of MRC. This is the hidden toxicity of the pulsatile DA replacement afforded by current, stand oral CD/LD therapies. The risk of these striatal changes rises with advancing disease and thus greater dopaminergic neuron loss. It also rises with the dose of LD. Moreover, the effective dose of CD/LD varies greatly from one patient to the next as a function of body weight and other factors—known and unknown. Research described above shows that it is essential that parkinsonian patients be given their optimally effective dose, but not higher, since doses higher than required, accelerate the development of MRCs. However, currently available oral CD/LD preparations do not allow convenient dose fractionation and therefore do not allow for precise and convenient dosing to best meet patient needs for safe and effective symptomatic relief.

Furthermore, currently available medications fail to address the medical needs of patients who require lower doses, such as children or those who are hypersensitive to LD.

In later stage individuals, with their massive loss of DA neurons and their capacity to store DA, currently available drugs and administration schedules stimulate striatal DA receptors in a non-physiologic, pulsatile manner. Long-term, periodic, high-intensity stimulation of these receptors inevitably leads to striatal changes that favor the appearance of MRCs. Thus, there is a progressive shortening of response duration, narrowing of the therapeutic window, and unrelenting involuntary movement affecting limbs, trunk and face that appear in nearly 50% of patients within 5 years and in some 90% within 10 years of treatment initiation. Ultimately, these MRCs become more disabling than the original parkinsonian symptoms.

The present invention is based on the concept that the frequent delivery of small precise oral doses of CD/LD can simulate the continuous intravenous administration of LD, thus overcoming the aforementioned dangers of the current CD/LD treatment.

In fact, it has been found that, by using a pharmaceutical unit form consisting of a multiscore tablet, said tablet comprising a pharmaceutical composition comprising CD/LD 25 mg/100 mg in admixture with a pharmaceutical carrier, and being divided, by two or three scores, in three or four sections, each section thereof comprising, respectively, CD/LD 8.(3) mg/33.(3) mg and CD/LD 6.25 mg/25 mg it is possible to administer frequent, predetermined single doses that are able to slow the progression of the disease in early stage patients and to alleviate the MRCs in advanced PD patients.

Surprisingly, it has also been found that such a frequent administration of CD/LD reduces the need for entacapone. This is advantageous because, although entacapone given together with CD/LD prolongs the duration of each dose of LD, this occurs in association with a deleterious increase in peak of LD.

Thus, the present invention provides a method for the treatment of PD and LD-requiring disorders in a patient in need of said treatment, while concurrently inhibiting or alleviating MRCs, which comprises treating said patient with a CD/LD single oral dose selected from the group consisting of 6.25 mg/25 mg, 8.(3) mg/33.(3) mg, 12.5 mg/50 mg, 16. (6) mg/66. (6) mg, 18.75 mg/75 mg, 25 mg/100 mg, 31.25 mg/125 mg, and 33. (3) mg/133. (3) mg from 5 times to 9 times per day The present invention also provides a new pharmaceutical unit form consisting of a multiscore tablet, said tablet comprising a pharmaceutical composition comprising CD/LD 25 mg/100 mg in admixture with a pharmaceutical carrier, and being divided, by two or three scores, in three or four sections, each section thereof comprising, respectively, CD/LD 8.(3) mg/33.(3) mg, and CD/LD 6.25 mg/25 mg.

In addition, the scores of the top layer penetrate the bottom inert layer, sufficiently to allow convenient splitting by a patient, but not to introduce superfluous fragility that favors spontaneous fracture, and without fully cutting it.

Herein below, said bilayered, deeply scored, multiscore tablet will be referred to as "DopaSnap" because its sections can be easily and precisely divided out without any loss of the CD and LD active principles. The DopaSnap tablet can be manufactured according to the process described in US 2008/0233189, the entire disclosure of which is incorporated herein by reference. It is designed only for the treatment of PD with the precise intent of alleviating the toxicity associated with all existing oral CL/LD formulations, i.e. the induction of MRCs.

Accordingly, the invention provides a three-score/four section, bilayered tablet formed by a top, scored layer, comprising a pharmaceutical composition comprising, as active ingredients, CD, in a total amount of 25 mg, and LD, in a total amount of 100 mg, in admixture with a pharmaceutical carrier, adjoined to an inert layer comprising a pharmaceutical carrier without active ingredient, each of the four sections of said tablet comprising a CD/LD unit dose having 6.25 mg/25 mg, As set forth above, unexpectedly, DopaSnap mimics the continuous, optimal-dose, intravenous administration of LD, by delivering frequent, small precise doses of CD/LD. Thus, LD plasma concentrations remain within the physiologic or "normal function" range and thus helping to avoid both dyskinesia and end-of-dose wearing off.

DopaSnap, seeks to effectively address the critical medical need of most parkinsonian patients to increase the precision and continuity of LD dosing and thus bring greater antiparkinsonian relief with less disabling adverse responses to all PD patients.

DopaSnap, designed and constructed for convenience in parkinsonian hands, takes a substantial stride towards enabling the benefits of the frequent administration of optimal dose CD/LD. After nearly 50 years of waiting, the medical needs of the PD patient at all stages of disease can be more adequately met.

DETAILED DESCRIPTION

The present invention provides
a method for the treatment of PD and related LD-requiring disorders, with concurrent prevention or treatment of MRCs, in a patient in need of said treatment, which comprises administering to said patient a CD/LD single dose selected from the group consisting of 6.25 mg/25 mg, 8.(3) mg/33.(3) mg, 12.5 mg/50 mg, 16.(6) mg/66.(6) mg, 18.75 mg/75 mg, 25 mg/100 mg, 31.25 mg/125 mg, and 33.(3) mg/133.(3) mg from 5 times to 9 times per day;
a pharmaceutical unit form consisting of a multiscore tablet comprising a pharmaceutical composition comprising CD/LD 25 mg/100 mg in admixture with a pharmaceutical carrier, and divided, by two or three scores, in three or four sections, each section comprising, respectively, CD/LD 8.(3) mg/33.(3) mg, and CD/LD 6.25 mg/25 mg;
the use of CD and LD for the preparation of a medicament for the treatment of PD, with concurrent prevention or treatment of MRCs, said medicament consisting of a multiscore tablet comprising a pharmaceutical composition comprising CD/LD 25 mg/100 mg in admixture with a pharmaceutical carrier, and divided, by two or three scores, in three or four sections, each section comprising, respectively, CD/LD 8.(3) mg/33.(3) mg, and CD/LD 6.25 mg/25 mg.

According to a first aspect, the present invention provides a tool for an easy realization of a new protocol for treating patients suffering from PD by concurrently preventing or treating MRCs.

Said new protocol provides a method for the treatment of Parkinson's disease in a patient in need of said treatment, while concurrently preventing or treating MCCs, which comprises treating said patient with a CD/LD single dose selected from the group consisting of 6.25 mg/25 mg, 8.(3) mg/33.(3) mg, 12.5 mg/50 mg, 16.(6) mg/66.(6) mg, 18.75 mg/75 mg, 25 mg/100 mg, 31.25 mg/125 mg, and 33.(3) mg/133.(3) mg, from 5 times to 9 times per day.

The new protocol is assured by using a pharmaceutical unit form consisting of a multiscore tablet comprising a pharmaceutical composition comprising CD/LD 25 mg/100 mg in admixture with a pharmaceutical carrier, and divided, by two or three scores, in three or four sections, each section comprising, respectively, CD/LD 8.(3) mg/33.(3) mg, and CD/LD 6.25 mg/25 mg, thus allowing the administration of one or more unit doses of CD/LD 6.25 mg/25 mg or. 8.(3) mg/33.(3) mg, Said single dose is being selected from the group consisting of from one section, two sections, three sections, the whole tablet and the whole tablet plus one section or more sections of a second bilayered tablet as described above. In the case of a three-score tablet, three sections correspond to the whole tablet.

The treatment of early stage PD is typically initiated with CD/LD (DopaSnap) at an unit dose of 6.25/25 mg or 8.(3) mg/33.(3) mg, according to the age and the weight of the patient, given orally every 3-4 hours while awake, over a period of 16-18 hours. For these early stage patients, the above CD/LD 6.25 mg/25 mg or 8.(3) mg/33.(3) mg unit dose is typically given at 5 to 6 times per day (from 31.25 mg/125 mg to 37.5 mg/150 mg per day or from 41.(6) mg/166.(6) mg to 50 mg/200 mg). This daily dose is subsequently titrated up over subsequent days and weeks to the lowest amount that optimally relieves motor symptoms or to a maximum single dose, usually in the range of from 16.(6) mg/66.(6) mg to 33.(3) mg/133.(3) mg, corresponding to a daily dose of from 83.(3) mg/666.(6) mg to 166.(6)/800 mg, normally in the range of from 18.75 mg/75 mg to 31.25 mg/125 mg, corresponding to a daily dose of from 93.75 mg/375 mg to 187.5 mg/750 mg. or from per single dose.

However, large inter-patient differences are not unexpected. Motor symptom relief involves the amelioration of parkinsonian tremor, rigidity, hypokinesia as well as difficulty with gait and balance. In some patients, the optimal dose of LD (in DopaSnap) may be as low as 25 mg or 50 mg, depending on such factors as body size and drug tolerance. Once patients have reached their optimal dose, they ordinarily continue treatment at that dose until symptoms change in ways that require dose adjustment. In some individuals dose adjustments are required throughout the day depending on such factors as food ingestion and activity status.

Within a year or two of treatment initiation, patients will be benefitted by shifting to a more frequent dosing schedule in order to maintain more constant brain dopamine levels and avoid both high peaks just after dosing and low troughs between dosing. Replacing brain dopamine in this more physiologic manner has been shown to delay the onset and reduce the severity of motor response complications. This is a syndrome, which occurs in some 40% of all PD patients after 5 years of dopaminergic treatment and in nearly 80% within 10 years is manifested by response fluctuations and abnormal involuntary movements which can become as disabling as the parkinsonian symptoms themselves.

The rise in the LD dose/motor response relation with disease progression intensifies the need for precise dosing afforded by DopaSnap in late stage patients.

The treatment of middle and late stage parkinsonian patients thus generally focuses on attempts to ameliorate the severely dysfunctional effects of motor complications. It has been shown that the constant administration of optimal-dose LD can rapidly reduced or even abolish these complications. With DopSnap treatment it becomes easy to take relatively low, frequent doses, for example LD single doses of from 25 mg to 125 mg every 90 min to 125 mg every 2 hours, that simulate constant infusion therapy. Generally, LD doses in the 75 mg to 125 mg range given every 2 hours (8-9 times over 16 hours) provide the best results, although wide inter- and intra-patient variability occurs. For example, in the late stage of PD, over 16 hours, a DopaSnap single dose of from 18.75 mg/75 mg to 31.25 mg/125 mg) every two hours provides a CD/LD daily dose of from 168 mg/675 mg to 281.25 mg/1125 mg allowing the prevention or treatment of MRCs.

According to an embodiment, the present invention provides a three-score/four section, bilayered tablet formed by a top, scored layer comprising a pharmaceutical composition comprising, as active ingredients, CD, in a total amount of 25 mg, and LD, in a total amount of 100 mg, in admixture with a pharmaceutical carrier for immediate release, adjoined to an inert bottom layer comprising a pharmaceutical carrier without active ingredient, each of the four sections of said top layer of said tablet comprising a CD/LD amount of 6.25 mg/25 mg.

Each DopaSnap tablet is triple-scored for ease of fractionated dosing and may be used whole (25/100 of CD/LD) or divided into 6.25/25 mg, 12.5/50 mg or 18.75 mg/75 mg CD/LD doses. The deep scoring permits tablet segments to be easily snapped apart manually without cutting instruments. Ease of fractionation is essential for elderly, motor-impaired patients.

DopaSnap tablets employ bilayered, deeply scored design. The top layer contains CD/LD and is pre-divided by 3 deep scores during the manufacturing process to provide exact doses. The bottom layer does not contain active drug; it provides mechanical stability and serves as the break region when splitting the tablet.

Accordingly, in the top layer, CD and LD are formulated with the calculated amount of CD and the calculated amount of LD active ingredients in admixture with a conventional pharmaceutical acceptable carrier in an immediate release formulation. Said calculated amount of the active ingredients in said top layer assures
   (a) a total CD amount per tablet of 25 mg; and
   (b) a total LD mount per tablet of 100 mg.

The bottom, inert layer that only serves for a precise splitting of single sections, without any loss of active ingredients is a formulation of a conventional pharmaceutical carrier, preferably the same as that of the top layer, without active ingredient Two or three scores divide the top layer in three or four sections, each containing 8.(3) mg CD and 33.(8) LD and, respectively, 6.25 mg CD and 25 mg LD and penetrate the bottom layer without cutting it, thus allowing the perfect splitting of the desired number of sections.

The pharmaceutical carriers include starches, cellulose and derivatives thereof; silica gel, microsilica gel; lubricants such as talc, stearic acid or magnesium stearate; diluents such as talc, powdered cellulose, lactose, starches such as maize or corn starch, pregelatinized starch, mannitol, sorbitol; disaggregating agents such as microcrystalline cellulose, low substituted hydroxypropylcellulose, or crospovidone; lubricants such as polyethylene glycol or magnesium stearate; ligands such as methylcellulose, sodium carboxymethylcellulose, alginic acid, alginates; sweeteners, such as sucrose, dextrose, mannitol, saccharin; or flavoring agents such as natural or synthetic oils.

Normally, layer (a), containing the calculated amount of the active ingredients in admixture with a binder, such as starch, starch past, pregelatinized starch or povidone, giving cohesiveness to the powder; a disintegrating agent such as crospovidone, cellulose, microcrystalline cellulose (MCC, for example PH-200, PH-102 or PH103 or PH-301) low substituted hydroxypropylcellulose, or carboxymethyl cellulose, facilitating the breakup of the tablet, or section(s), after oral administration; and a lubricant, such as talc, stearic acid or magnesium stearate, preventing the formation of strong compacts, thus favoring the final compression phase of the tablet manufacturing process.

Layer (b) is formed by a pharmaceutical carrier, preferably the same as that of layer (a), but without the active ingredients.

DopaSnap may also be manufactured as an orally disintegrable tablet by using excipients such as MCC PH-102 or PH-301, microsilica gel, low-substituted hydroxypropylcellulose in both the active layer (a) and the inert layer (b), for example as described in CN100384411(C).

The tablets are preferably manufactured using a first granulation (preferably wet granulation) comprising CD/LD and a second (preferably wet) granulation compounding the pharmaceutical carrier, preferably the same as that of the active layer.

In particular, for the manufacture of the three score, four sections tablet of the present invention, the active layer is separately prepared by mixing the calculated amount of CD and LD with a binder such as povidone or pregelatinized starch. Water is added to the mixture and said mixture is submitted to wet granulation. After a possible dying of the granulate in a fluidized bed dyer, the mass is submitted to a screening through an 18.mesh screen and milled. The mixture thus obtained is blended with a disintegrating agent such as cellulose or microcrystalline cellulose, and with a lubricant, such as stearic acid or with al earth-metal salt stearate, preferably magnesium stearate, preferably in a V-blender.

Separately, the calculated amount of a binder, a disintegrating agent and a lubricant, preferably the same used in the preparation of the blended mixture for the active layer, is submitted to blending, preferably in a V-blender.

The tablets are only manufactured on a Bi-Layer Tablet Compression machine. The manufacture method utilizes a protuberance known as an embossing that rises from the lower punch of a tablet die in said tablet compression machine. The active, above granulation containing the calculated amount of CD/LD enters the die, forms a layer above the highest point of said embossing, and is tamped by the upper punch. The inert, second granulation enters said die on top of said first granulation, is tamped by the upper punch, and then the tablet is compressed by the upper punch so that said compression pushes said first granulation below the highest points of said embossing. Said embossing occupies a position on the lower punch trisecting or quadrisecting said lower punch, so that said compression causes the active layer to be divided into three or four sections.

As set forth above, the present invention provides a tool for an easy realization of a new protocol for treating patients suffering from PD by concurrently preventing or treating MRCs.

Said new protocol provides a method for the treatment of Parkinson's disease in a patient in need of said treatment, while concurrently preventing or treating MCCs, which comprises treating said patient with a CD/LD single dose selected from the group consisting of 6.25 mg/25 mg, 12.5 mg/50 mg, 18.75 mg/75 mg, 25 mg/100 mg and 31.25 mg/125 mg, from 5 times to 9 times per day, said single dose being selected from the group consisting of from one section, two section, three sections, the whole tablet and the whole tablet plus one section of a second of the three-score/four section, bilayered tablets as described above.

The treatment of early stage PD is typically initiated with CD/LD (DopaSnap) at a dose of 6.25/25 mg given orally every 3-4 hours while awake, over a period of 16-18 hours. For these early stage patients, the above CD/LD 6.25 mg/25 mg unit dose is typically given at 5 to 6 times per day (from 31.25 mg/125 mg to 37.5/150 mg per day). This dose is subsequently titrated up over subsequent days and weeks to the lowest amount that optimally relieves motor symptoms or to a maximum, usually in the range of about 18.75 mg/75 mg to 31.25 mg/125 mg per dose. However, large inter-patient differences are not unexpected. Motor symptom relief involves the amelioration of parkinsonian tremor, rigidity, hypokinesia as well as difficulty with gait and balance. In some patients, the optimal dose of LD (in DopaSanp) may be as low as 25 mg or 50 mg, depending on such factors as body size and drug tolerance. Once patients have reached their optimal dose, they ordinarily continue treatment at that dose until symptoms change in ways that require dose adjustment. In some individuals dose adjustments are required throughout the day depending on such factors as food ingestion and activity status.

Within a year or two of treatment initiation, patients will be benefitted by shifting to a more frequent dosing schedule in order to maintain more constant brain dopamine levels and avoid both high peaks just after dosing and low troughs between dosing. Replacing brain dopamine in this more physiologic manner has been shown to delay the onset and reduce the severity of motor response complications. This is a syndrome, which occurs in some 40% of all PD patients after 5 years of dopaminergic treatment and in nearly 80% within 10 years is manifested by response fluctuations and abnormal involuntary movements which can become as disabling as the parkinsonian symptoms themselves.

The rise in the LD dose/motor response relation with disease progression intensifies the need for precise dosing afforded by DopaSnap in late stage patients.

The treatment of middle and late stage parkinsonian patients thus generally focuses on attempts to ameliorate the severely dysfunctional effects of motor complications. It has been shown that the constant administration of optimal-dose LD can be rapidly reduced or even abolish these complications. With DopSnap treatment it becomes easy to take relatively low, frequent doses, for example from 25 to 125 mg every 90 min to 125 mg every 2 hours, that simulated constant infusion therapy. Generally, LD doses in the 75 to 125 mg range given every 2 hours (8-9 times over 16 hours) provide the best results, although wide inter- and intra-patient variability occurs.

Example 1

Preparation of a Carbidopa/Levodopa 25/100 Tablet

A tablet comprising an inert layer with a superimposed, adjoined active layer, formed by four unitary segments each containing equal amounts of carbidopa/levodopa 6.25 mg/25 mg has the following characteristics:

Tablet Size: 0.675"×0.332" (corresponding to 17.145 mm×8.433 mm)
Thickness: 4 mm
Tablet Weight: 600 mg
Active Layer: 250 mg
Inert layer: 350 mg.

The active layer (also referred to as top layer) has the formulation given in Table 1 below.

TABLE 1

| | Material | mg/Dose | % |
|---|---|---|---|
| Internal Phase | Carbidopa[1] | 25 | 10.0 |
| | Levodopa | 100 | 40.0 |
| | Pre-Gelatinized Starch 1500 | 25 | 10.0 |
| | Purified Water | — | — |
| External Phase | Microcrystalline Cellulose PH-200 | 72.5 | 29.0 |
| | Pre-Gelatinized Starch 1500 | 25 | 10.0 |
| | Magnesium stearate | 2.5 | 1.0 |
| Total: | | 250 | 100.0 |

[1]Weight adjusted based on Certificate of Analysis (COA) Loss on Drying.

Said active layer is manufactured by the following 6-step process.

1. Wet granulation process with high shear or top spray fluidized granulation. Mixing Carbidopa, Levodopa and the Pre-Gelatinized Starch 1500, adding purified water.
2. Drying wet granules from 1 by fluidized bed dryer.
3. Milling dried granules from 2 by Co-mil with 1000 micron screen.
4. Calculation and weigh-off the external excipients based on the weight of milled dried granules from 3.
5. Mixing external phase, Microcrystalline Cellulose PH-200, Pre-Gelatinized Starch 1500 and magnesium stearate, preferably in a V-blender.
6. Discharge final blend. Ready for compression.

The inert layer (also referred to as bottom segment) has the formulation given in Table 2 below.

TABLE 2

| Material | mg/Dose | % |
|---|---|---|
| Microcrystalline Cellulose PH-200 | 140 | 40.0 |
| Pre-Gelatinized Starch 1500 | 206.5 | 59.0 |
| Magnesium Stearate | 3.5 | 1.0 |
| Total: | 350 | 100% |

Said inert layer is manufactured by a direct blending process: (a) weigh-off excipients; (b) blending Microcrystalline Cellulose PH-200, Pre-Gelatinized Starch 1500 and magnesium stearate, preferably in a V-blender, (c) discharge final blend. Ready for compression. The compression is made by using a bi-layer press machine fitted with the appropriate tooling and compress into tablets.

Example 2

Preparation of a Carbidopa/Levodopa 25/100 Tablet

A tablet comprising an inert layer with a superimposed, adjoined active layer, formed by four unitary segments each containing equal amounts of carbidopa/levodopa 6.25 mg/25 mg has the following characteristics:
Tablet Size: 0.7480"×0.2920" (corresponding to 19 mm×7.417 mm)
Thickness: 4.0 mm
Tablet Weight: 640 mg
Active Layer: 310 mg
Inert layer: 330 mg 1. Active Layer: The active layer (also referred to as top layer) has the following formulation qualitative and quantitative composition given in Table 1 below.

TABLE 1

| | Material | mg/Dose | % |
|---|---|---|---|
| Internal Phase | Carbidopa | 26.99* | 8.71 |
| | Levodopa | 100.0 | 32.26 |
| | Microcrystaliine Cellulose, PH 102 | 8.01 | 2.58 |
| | Pre-Gelatinized Starch 1500 | 15.00 | 4.84 |
| | Purified Water | 0.0 | 0.0 |
| External Phase | Microcrystalline Cellulose PH-200 | 156.90 | 50.61 |
| | Magnesium stearate | 3.10 | 1.000 |
| Total weight of Active Layer: | | 310.00 | 100.0 |

*Equivalent to 25 mg label claim for Carbidopa (a monohydrate).

Active layer is manufactured by Wet granulation process with high shear granulation and followed by Dry mixing process with the following 6-step process.
1. Mix Carbidopa, Levodopa, Microcrystalline Cellulose PH 102 and the Pre-Gelatinized Starch 1500 together and granulate by adding a suspension of Starch 1500 in purified water.
2. Dry the wet granules in a fluidized bed dryer.
3. Mill dried granules from step 2 by Co-mill with 1000 micron screen.
4. Calculate and weigh-off the external phase excipients based on the weight of milled dried granules obtained from step 3.
5. Mixing external phase (MCC PH 102) and Combo drug granules to a specified time preferably in a V-blender and finally lubricate the blend with magnesium stearate.
6. Discharge final blend. Ready for compression, along with Placebo or Inactive or Inert Layer.

2. Placebo or Inactive or Inert Layer: The inert layer (also referred to as bottom segment) has the following formulation qualitative and quantitative composition given in Table 2 below.

TABLE 2

| Material | mg/Dose | % |
|---|---|---|
| Microcrystalline Cellulose PH-102 | 326.70 | 99.0 |
| Magnesium Stearate | 3.30 | 1.0 |
| Total weight of Inert Layer | 330.00 | 100.0 |

Said inert layer is manufactured by a direct blending process:
(a) Weigh-off excipients;
(b) Blend Microcrystalline Cellulose PH-102 along with magnesium stearate, preferably in a V-blender, for a specified time.
(c) Discharge final blend. Ready for compression.

3. Tablet compression: The compression is made by using a bi-layer press machine fitted with the appropriate tooling and compress into tablets.

REFERENCES

Chase T N1, Engber T M, Mouradian M M. Palliative and prophylactic benefits of continuously administered dopaminomimetics in Parkinson's disease. Neurology. 1994; 44:15-8.

Chase T N1, Mouradian M M, Engber T M. Motor response complications and the function of striatal efferent systems. Neurology. 1993; 43: S23-7.

Chase T N1, Baronti F, Fabbrini G, Heuser I J, Juncos J L, Mouradian M M. Rationale for continuous dopaminomimetic therapy of Parkinson's disease. Neurology. 1989; 9l:S7-10.

Mouradian M M1, Juncos J L, Fabbrini G, Chase T N. Motor fluctuations in Parkinson's disease: pathogenetic and therapeutic studies. Ann Neurol. 1987; 22:475-9.

Bibbiani F[1], Costantini L C, Patel R, Chase T N. Continuous dopaminergic stimulation reduces risk of motor complications in parkinsonian primates. Exp Neurol. 2005 March; 192(1):73-8.

Mouradian M M[1], Heuser I J, Baronti F, Chase T N. Modification of central dopaminergic mechanisms by continuous levodopa therapy for advanced Parkinson's disease. Ann Neurol. 1990; 27:18-23.

Stella M. Papa Thomas M. Engber Anne M. Kask Thomas N. Chase Motor fluctuations in levodopa treated parkinsonian rats: relation to lesion extent and treatment duration. Brain Research 1994; 662:69-74.

The invention claimed is:
1. A method for the treatment of Parkinson's disease or related levodopa (LD)-responsive disorders, comprising orally administering to a patient in need thereof, a composition comprising carbidopa/levodopa (CD/LD) at a dose which simulates continuous intravenous administration of LD when administered up to 9 times per day,
wherein the dose comprises CD in an amount of 25 mg or less and LD in an amount of 100 mg or less, and
wherein said composition does not comprise entacapone.
2. The method of claim 1, wherein the dose comprises CD in an amount of 25 mg and LD in an amount of 100 mg.

3. The method of claim 1, wherein the dose comprises CD in an amount of 18.75 mg or less and LD in an amount of 75 mg or less.

4. The method of claim 1, wherein the dose comprises CD in an amount of 12.5 mg or less and LD in an amount of 50 mg or less.

5. The method of claim 1, wherein the dose comprises CD in an amount of 6.25 mg or less and LD in an amount of 25 mg or less.

6. The method of claim 1, wherein said patient is a newly diagnosed patient at the initial stage of Parkinson's disease.

7. The method of claim 1, wherein said patient is a patient at the middle or late stage of Parkinson's disease.

8. The method of claim 1, wherein said patient is a parkinsonian patient previously administered a standard treatment with carbidopa/levodopa.

9. The method of claim 8, wherein said patient suffers from motor response complications.

10. The method of claim 1, wherein the CD/LD is present in a multiscore tablet comprising a fully scored top layer divided by two or three scores providing three or four sections, wherein each section comprises CD/LD, and a bottom inert layer partially penetrated by each of the scores.

11. The method of claim 10, wherein a total amount of CD/LD in the multiscore tablet is 25 mg or less of carbidopa and 100 mg or less of levodopa, wherein the top layer of the tablet is divided by three scores providing four sections, and wherein the total amount of CD/LD is evenly divided between each section of the tablet.

12. The method of claim 10, wherein one to four sections is administered as the dose 5 to 9 times per day.

13. The method of claim 10, wherein one to four sections is administered as the dose 5 to 6 times per day.

14. The method of claim 1, wherein the dose of LD provides a constant plasma concentration range of the LD for full efficacy with no motor response complications.

15. A method of treating or alleviating motor response complications related to Parkinson's disease or related levodopa (LD)-responsive disorder, comprising orally administering to a patient in need thereof, a composition comprising carbidopa/levodopa (CD/LD) at a dose which simulates continuous intravenous administration of LD when administered up to 9 times per day,
wherein the dose comprises CD in an amount of 25 mg or less and LD in an amount of 100 mg or less, and
wherein said composition does not comprise entacapone.

16. The method of claim 15, wherein the dose comprises CD in an amount of 25 mg and LD in an amount of 100 mg.

17. The method of claim 15, wherein the dose comprises CD in an amount of 18.75 mg or less and LD in an amount of 75 mg or less.

18. The method of claim 15, wherein the dose comprises CD in an amount of 12.5 mg or less and LD in an amount of 50 mg or less.

19. The method of claim 15, wherein the dose comprises CD in an amount of 6.25 mg or less and LD in an amount of 25 mg or less.

20. The method of claim 15, wherein said patient is a newly diagnosed patient at the initial stage of Parkinson's disease.

21. The method of claim 15, wherein said patient is a patient at the middle or late stage of Parkinson's disease.

22. The method of claim 15, wherein the CD/LD is present in a multiscore tablet comprising a fully scored top layer divided by two or three scores providing three or four sections, wherein each section comprises CD/LD, and a bottom inert layer partially penetrated by each of the scores.

23. The method of claim 22, wherein a total amount of CD/LD in the multiscore tablet is 25 mg or less of carbidopa and 100 mg or less of levodopa, wherein the top layer of the tablet is divided by three scores providing four sections, and wherein the total amount of CD/LD is evenly divided between each section of the tablet.

24. The method of claim 22, wherein one to four sections is administered as the dose 5 to 9 times per day.

25. The method of claim 22, wherein one to four sections is administered as the dose 5 to 6 times per day.

26. The method of claim 15, wherein the dose of LD provides a constant plasma concentration range of the LD for full efficacy with no motor response complications.

27. A method for the treatment of Parkinson's disease or related levodopa (LD)-responsive disorders, comprising orally administering to a patient in need thereof, a composition comprising carbidopa/levodopa (CD/LD) at a dose which simulates continuous intravenous administration of LD, 4 times per day,
wherein the dose comprises CD in an amount of 12.5 mg and LD in an amount of 50 mg.

28. The method of claim 27, wherein said composition does not comprise entacapone.

29. The method of claim 27, wherein the dose comprises CD in an amount of 6.25 mg or less and LD in an amount of 25 mg or less.

30. The method of claim 27, wherein said patient is a newly diagnosed patient at the initial stage of Parkinson's disease.

31. The method of claim 27, wherein said patient is a patient at the middle or late stage of Parkinson's disease.

32. The method of claim 27, wherein said patient is a parkinsonian patient previously administered a standard treatment with carbidopa/levodopa.

33. The method of claim 32, wherein said patient suffers from motor response complications.

34. The method of claim 27, wherein the CD/LD is present in a multiscore tablet having a fully scored top layer divided by two or three scores providing three or four sections, wherein each section comprises the dose of CD/LD, and a bottom inert layer partially penetrated by each of the scores.

35. The method of claim 34, wherein a total amount of CD/LD in the multiscore tablet is 25 mg or less of carbidopa and 100 mg or less of levodopa, wherein the total amount of CD/LD is evenly divided between each section of the tablet.

36. A method for the treatment of Parkinson's disease or related levodopa (LD)-responsive disorders, comprising orally administering to a patient in need thereof, a composition comprising carbidopa/levodopa (CD/LD) at a dose which simulates continuous intravenous administration of LD when administered up to 9 times per day,
wherein the dose is selected from the group consisting of carbidopa-6.25 mg/levodopa-25 mg, carbidopa-8.3 mg/levodopa-33.3 mg, carbidopa-12.5 mg/levodopa-50 mg, carbidopa-16.6 mg/levodopa-66.6 mg, carbidopa-18.75 mg/levodopa-75 mg, carbidopa-25 mg/levodopa-100 mg,
wherein the CD/LD are present in a multiscore tablet comprising a fully scored top layer divided by two or three scores providing three or four sections, wherein each section comprises the dose of CD/LD, and a bottom inert layer partially penetrated by each of the scores, and wherein a total amount of CD/LD in the multiscore tablet is 25 mg of carbidopa and 100 mg of levodopa, wherein the total amount of CD/LD is evenly divided between each section of the tablet, wherein the composition does not comprise entacapone.

37. The method of claim 36, wherein the dose is carbidopa-6.25 mg/levodopa-25 mg and wherein the total amount of CD/LD in the multiscore tablet is 25 mg of carbidopa and 100 mg of levodopa.

38. The method of claim 36, wherein said patient is a newly diagnosed patient at the initial stage of Parkinson's disease.

39. The method of claim 36, wherein said patient is a patient at the middle or late stage of Parkinson's disease.

40. The method of claim 36, wherein said patient is a parkinsonian patient previously administered a standard treatment with carbidopa/levodopa.

41. The method of claim 40, wherein said patient suffers from motor response complications.

42. The method of claim 36, wherein one or more sections is administered 5 to 9 times per day.

43. The method of claim 36, wherein one or more sections is administered 5 to 6 times per day.

44. The method of claim 36, wherein the dose of LD provides a constant plasma concentration range of the LD for full efficacy with no motor response complications.

\* \* \* \* \*